United States Patent [19]

Nelson

[11] Patent Number: 5,304,061
[45] Date of Patent: Apr. 19, 1994

[54] BRACKET HEIGHT POSITIONING DIMPLE

[76] Inventor: Edward J. Nelson, 1907 N. Quincy St., Arlington, Va. 22207

[21] Appl. No.: 876,334

[22] Filed: Jun. 1, 1992

[51] Int. Cl.$^5$ .................................. A61C 3/00
[52] U.S. Cl. .......................... 433/8; 433/9; 433/24
[58] Field of Search ............ 433/8, 9, 10, 24, 72, 433/3

[56] References Cited

U.S. PATENT DOCUMENTS

| | | | |
|---|---|---|---|
| 3,871,098 | 3/1975 | Dean | 433/3 |
| 4,117,596 | 10/1978 | Wallshein | 433/9 |
| 4,134,208 | 1/1979 | Pearlman | 433/8 |
| 4,659,309 | 4/1987 | Merkel | 433/9 |
| 4,799,882 | 1/1989 | Kesling | 433/8 |
| 5,022,854 | 6/1991 | Broughton et al. | 433/8 |
| 5,055,038 | 10/1991 | Ronay et al. | 433/24 |
| 5,125,831 | 6/1992 | Pospisil | 433/8 |
| 5,154,606 | 10/1992 | Wildman | 433/8 |
| 5,226,814 | 8/1993 | Allen | 433/15 |

OTHER PUBLICATIONS

OIS Orthodontics Cataloge, Summe 1992, p. 42, "Boone Bracket Positioning Gauge".

Primary Examiner—Gene Mancene
Assistant Examiner—Cindy A. Cherichetti
Attorney, Agent, or Firm—Baker & Botts

[57] ABSTRACT

A cutout or dimple is provided in an orthodontic bracket and is sized to receive a projection of a measuring instrument to facilitate positioning of the bracket on a tooth. Preferably, the cutout is a conical dimple sized to receive the tip of a Boone gauge or other measuring instrument.

9 Claims, 2 Drawing Sheets

BRACKET HEIGHT POSITIONING DIMPLE

FIELD OF THE INVENTION

The invention relates to positioning of orthodontic brackets at a correct position on a tooth.

DETAILED DESCRIPTION OF THE PREFERRED EMBODIMENTS

Figure 1:
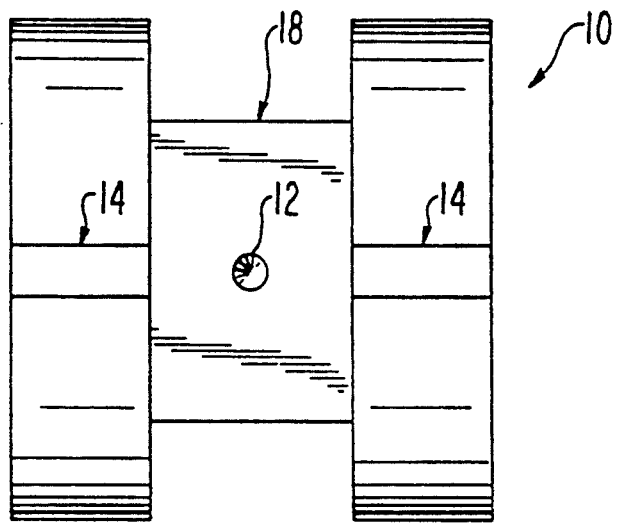
FIG. 1 is a frontal view of a siamese orthodontic bracket with the bracket height positioning dimple placed in the base of the bracket at the exact level of the orthodontic archwire slot.
Figure 2:
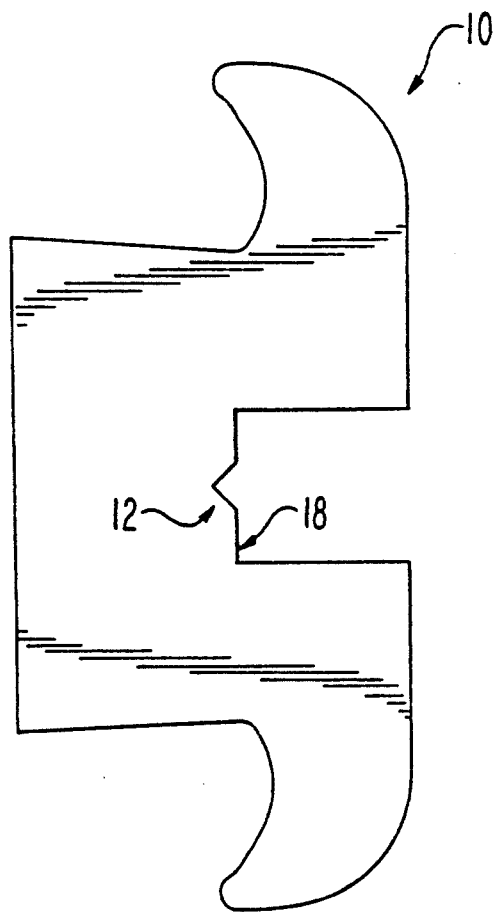
FIG. 2 is a profile view of a siamese orthodontic bracket with the bracket height positioning dimple placed in the base of the bracket at the exact level of the orthodontic archwire slot.
Figure 3:
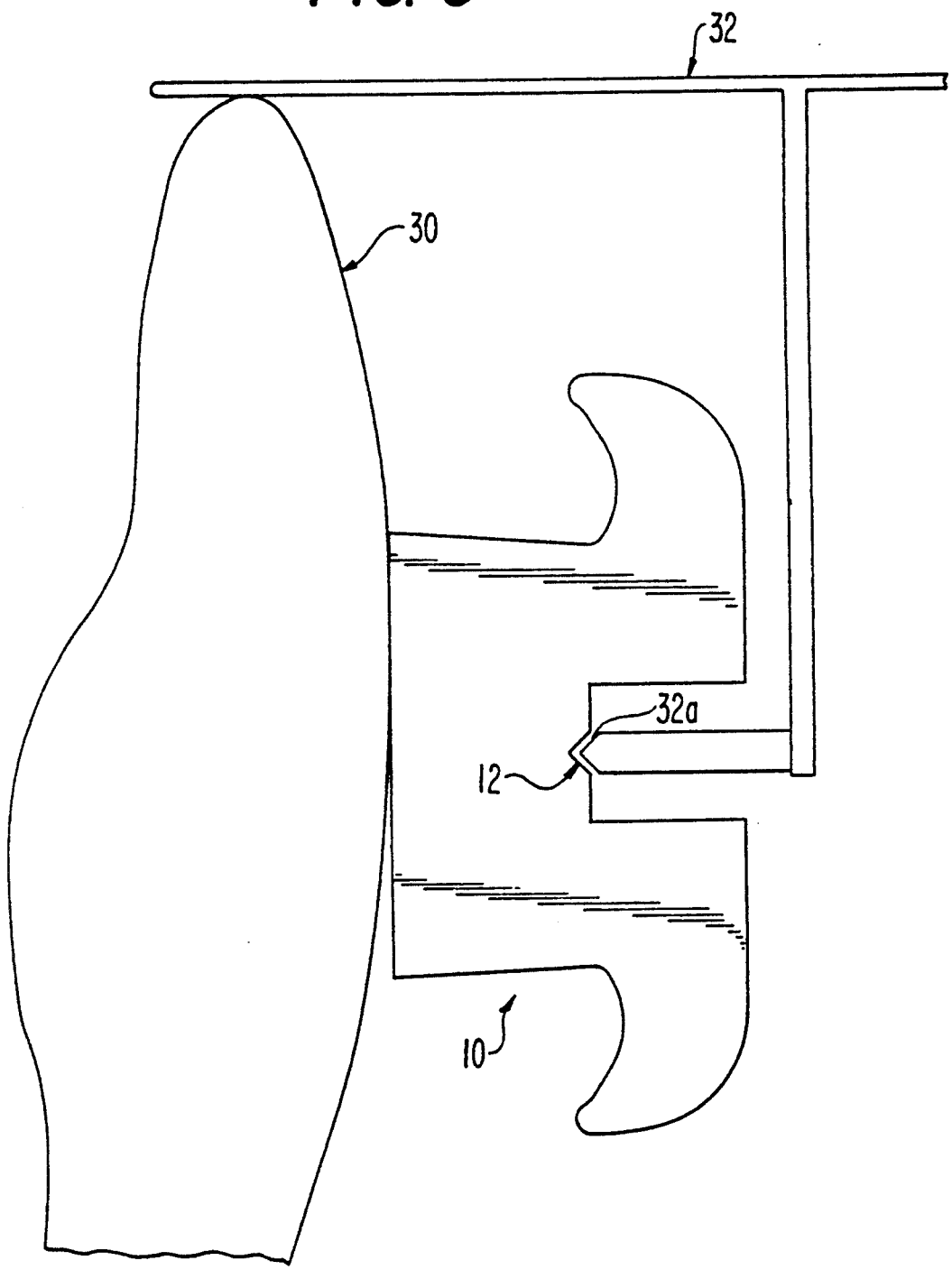
FIG. 3 is a profile view of an incisor tooth, an orthodontic bracket with the bracket height positioning dimple placed in the base at the level of the archwire slot, and an orthodontic bracket height measuring instrument being engaged into the dimple.

As shown in FIG. 1 and 2, for example, the invention relates to an orthodontic bracket 10, whether bonded or banded, including a device to help facilitate correct incisal-gingival or occlusal-gingival placement. The device is a small indentation (dimple) 12 in the base 18 of the bracket at the level where the archwire crosses. As shown in FIG. 1, the indentation 12 coincides with the level of the archwire slot 14. The indentation can be machined or cast into the orthodontic bracket. The indentation is sized to accept the tip of a Boone gauge or similar orthodontic bracket height measuring instrument. The size of the indentation can be variable if necessary, however a cone shaped indentation of 0.5 mm–1.0 mm. in diameter and 0.5 mm–1.0 mm. in depth is sufficient in order for one of these height measuring instruments to fit. As shown in FIG. 3, a bracket 10 is positioned on a tooth 30 by engaging a portion 32a of the bracket height measuring instrument 32 and the dimple 12.

I claim:

1. An orthodontic bracket comprising:
a base; projections extending from said base; an arch wire slot formed in said projections; and a cutout means formed in said base for receiving a portion of a measuring instrument and facilitating positioning of said bracket at a desired position on a tooth.

2. The orthodontic bracket of claim 1 wherein said cutout means is dimensioned to receive a tip of a Boone gauge.

3. The orthodontic bracket of claim 1 wherein said cutout comprises a conical cutout.

4. The orthodontic bracket of claim 3 wherein said conical cutout has a diameter substantially equal to 0.5–1.0 mm.

5. The orthodontic bracket of claim 3 wherein said cutout has a depth substantially equal to 0.5–1.0 mm.

6. The orthodontic bracket of claim 3 wherein said cutout has a diameter substantially equal to 0.5–1.0 mm and a depth substantially equal to 0.5–1.0 mm 7. An orthodontic bracket comprising:
a base; and a cutout means formed in said base for receiving a portion of a measuring instrument and facilitating positioning of said bracket at a desired position on a tooth, wherein said cutout means comprises a conical dimple.

8. The orthodontic bracket of claim 7 further comprising slot means for receiving an archwire and wherein said cutout means is located at a height substantially coincident with said slot means.

9. A method of positioning an orthodontic bracket on a tooth, wherein said bracket comprises a base comprising at least a first wall and having a cutout formed in said first wall; projections extending from said base; and an arch wire slot formed in the projections, said method comprising the steps of:

positioning a reference portion of a measuring instrument against a portion of said tooth to establish a reference level; and positioning a second portion of said measuring device, which is located a predetermined distance from said reference level and which comprises a projection, into said cutout to thereby facilitate positioning of said bracket on said tooth.

* * * * *